(12) United States Patent
Hunaidi

(10) Patent No.: US 6,561,032 B1
(45) Date of Patent: May 13, 2003

(54) NON-DESTRUCTIVE MEASUREMENT OF PIPE WALL THICKNESS

(75) Inventor: Osama Hunaidi, Ottawa (CA)

(73) Assignee: National Research Council of Canada, Ottawa (CA)

(*) Notice: Subject to any disclaimer, the term of this patent is extended or adjusted under 35 U.S.C. 154(b) by 0 days.

(21) Appl. No.: 09/570,922

(22) Filed: May 15, 2000

(51) Int. Cl.$^7$ .............................................. G01N 29/18
(52) U.S. Cl. ........................................ 73/597; 702/171
(58) Field of Search .................... 73/597, 598, 592, 73/622; 702/39, 170, 171

(56) References Cited

U.S. PATENT DOCUMENTS

| | | | |
|---|---|---|---|
| 5,531,099 A | 7/1996 | Russo | 73/40.5 |
| 5,581,037 A | 12/1996 | Kwun et al. | 73/623 |
| 5,965,818 A | 10/1999 | Wang | 73/598 |
| 5,970,434 A | 10/1999 | Brophy et al. | 702/170 |
| 6,000,288 A | 12/1999 | Kwun et al. | 73/597 |
| 6,035,717 A * | 3/2000 | Carodiskey | 73/597 |

FOREIGN PATENT DOCUMENTS

WO     98/19147     5/1998

OTHER PUBLICATIONS

"Dispersion of longitudinal waves propagating in liquid–filled cylindrical shells", Hegeon Kwun et al., Accoustical Society of America, 105(5), May 1999, pp. 2601–2611.

* cited by examiner

Primary Examiner—John E. Chapman
(74) Attorney, Agent, or Firm—Marks & Clerk

(57) ABSTRACT

The average wall thickness of a pipe carrying a fluid is determined by sensing disturbances in the pipe at two spaced locations, determining the propagation velocity of coupled propagation mode signals at low frequencies resulting from the disturbances, and calculating the average pipe wall thickness between the two locations from the propagation velocity and known constants for the pipe and fluid.

15 Claims, 1 Drawing Sheet

NON-DESTRUCTIVE MEASUREMENT OF PIPE WALL THICKNESS

FIELD OF THE INVENTION

This invention relates generally to the measurement of pipe wall thickness, and particularly to a method of measuring the average wall thickness of buried pipes, for example, municipal water pipes in a non-intrusive manner.

BACKGROUND OF THE INVENTION

Buried pipes, particularly municipal water pipes, deteriorate over time. In particular, buried pipes lose wall thickness as a result of corrosion and eventually fail leading to service disruption and economic loss. The pipes have to be periodically inspected and their structural capacity evaluated against design loads. Accurate information about pipe wall thickness is needed to determine the structural capacity.

Also, monitoring of wall thickness loss is needed to estimate the remaining service life of pipes, which is an important part of effective maintenance management systems of large pipe networks, for example, urban water distribution systems.

There is a need to measure the wall thickness of buried pipes in a nondestructive and non-intrusive way, that is without damaging the pipe and without taking it out of service.

Pipe wall thickness may be measured by obtaining pipe samples, known as coupons, and then measuring the thickness off-site using an ultrasonic gauge. This method provides only a discrete measurement of wall thickness at a specific point on the pipe. An alternative method for obtaining a continuous measurement of pipe wall thickness employs ultrasonic or magnetic flux leak sensors that are launched inside pipes using robots (known as pipeline pigs).

Obtaining pipe coupons is very expensive and requires excavating the pipe at several points. Also, thickness values based on the coupons may not be statistically representative of the overall condition of the pipe unless a very large number of coupons is obtained, which is often not practical.

Pipeline pigging requires taking the pipe out of service and cleaning the pipe before launching an inspection pig. It is mostly used for large diameter pipes with simple geometry, (i.e. no abrupt bends) such as oil and gas transmission pipelines. Also, data acquisition and analysis is very intensive and expensive. Pipeline inspection pigs are therefore not suitable for water distribution systems, which usually consist of small-diameter pipes forming networks that are very complex geometrically. Also, water pipes are usually filled with debris and have no pig launching stations.

Brophy et al., U.S. Pat. No. 5,970,434, discloses a method of measuring the wall thickness of a pipeline, wherein ultrasonic or magnetostrictive wave probes are used to analyze the dispersive behaviour of waves traveling in the tube wall volume. These waves are injected into the pipe at a first location and measurements are taken at a second location. Changes in cut-off frequency, according to Brophy, are related to pipe wall thickness. Brophy's method is designed for the testing of "U-shaped tubes" found industrial heat exchangers and will not work in municipal water systems since the ultrasonic waves would be damped too quickly as the ultrasonic waves attenuate very rapidly and would not therefore propagate over a sufficient distance to be useful for municipal water pipes. Also, most water systems contain pipes that are mechanically joined, and the waves would not propagate through the joints.

SUMMARY OF THE INVENTION

According to the present invention there is provided a method of measuring the wall thickness of a pipe carrying a fluid medium, comprising sensing disturbances in the pipe at two spaced locations, determining the propagation velocity of coupled propagation mode signals at low frequencies resulting from said disturbances, and calculating the average pipe wall thickness between said two locations from said propagation velocity and known constants for said pipe and fluid medium.

The coupled propagation velocity is typically in the range of 1000–1,300 m/s for metal pipes, and 300–500 m/s for plastic pipes. The invention is however applicable to other types of pipe material, such as concrete.

The advantage of using the coupled propagation mode, wherein propagation occurs both in the fluid and pipe wall, is that it is non-dispersive at low frequencies. By low frequencies, it is understood that the wavelength of the disturbances is large compared to the diameter of the pipe, typically five to ten times the pipe diameter. In coupled propagation mode, a signal propagating in the fluid medium continually excites the pipe wall, and vice versa. The two vibrational phenomena interact to propagate the wave along the pipe even past joints and other obstructions.

The locations may, for example, be spaced 100 meters apart. The difference between the times of arrival of a signal from a disturbance originating outside the two sensors permits the velocity of propagation to be calculated. In the coupled propagation mode, this velocity can be conveniently used to determine pipe wall thickness. At higher frequencies, dispersive effects and other factors make such a calculation much more complicated.

In accordance with the invention, the pipe wall thickness is determined from the average propagation velocity of low-frequency dynamic disturbances in the pipe, e.g. pressure fluctuation.

The propagation velocity can be obtained on-site non-destructively and non-intrusively based on the time shift (or lag) between vibration signals measured simultaneously at two separate points of the pipe.

Ambient noise in the pipe can be utilized as the vibration source. Alternatively, noise simulated by releasing pressurized fluid inside the pipe at an in-bracket or out-of-bracket point can be used, e.g., a fire hydrant in the case of wafer distribution pipes. Vibrations may be measured using a pair of accelerometers (or hydrophones) placed at two points that are a known distance apart and in direct contact with the pipe, for example, at control valves or fire hydrants.

The time shift between the measured signals is determined using the well-known time-of-flight method or the cross-correlation function calculated in the either of the time or frequency domains. The average propagation velocity in the pipe can then be calculated by dividing the sensor-to-sensor spacing by the time shift.

The propagation velocity depends on the type and size of pipe, i.e., its material, diameter and wall thickness. It can be calculated theoretically by the following equation:

$$c = c_o \sqrt{\frac{1}{[1 + a(D/e)(K_w/E_\rho)]}}$$

where c is the propagation velocity of leak signals in the pipe, $c_0$ is the propagation velocity of sound in an infinite body of water equal to $\sqrt{K_w/\rho}$, where $K_w$ is the bulk modulus of elasticity of water, ρ is density of water, $E_p$ is the modulus of elasticity of the pipe material, D is internal diameter of the pipe, e is the thickness of the pipe wall, and α is constant that depends on the constraints of longitudinal movement of the pipe (α equals 1 for pipes which are completely free, which is generally the case for pipes having expansion joints. This is normally the case for water distribution pipes).

The pipe wall thickness is back-calculated by substituting in the above equation the measured value of the propagation velocity and values of all other pipe parameters which are usually known. This pipe wall thickness determined in this manner represents an average value the pipe segment between the two points where vibration signals are measured.

The invention can also be used to determine the type of pipe. Sometimes, it is not known what type of pipes are buried, and by measuring the coupled mode propagation velocity it is possible to distinguish between the different types of pipe material, e.g., metallic vs. plastic.

The method is non-destructive and non-intrusive. All required measurements can be made from the ground surface without excavating the pipe or taking it out of service. The pipe wall thickness is an average value. The length of the pipe segment represented by this value can be arbitrarily chosen. Average thickness values are more appropriate and meaningful than discrete values for evaluating the residual life of pipes needed for the long-term planning of rehabilitation and replacement needs. The residual life depends on the overall condition of the pipe rather than on localized defects or thickness variation.

The invention is applicable to both metal and plastic pipes. In the case of plastic pipes, the vibrational frequencies are generally subsonic, whereas in the case of metal pipe they range up to about 800 Hz.

The proposed method is easy to implement, for example, in conjunction with routine leak detection surveys. Also, it does not require a high level of operator skill.

BRIEF DESCRIPTION OF THE DRAWINGS

The invention will now be described in more detail by way of example only, with reference to the accompanying drawings, in which.

DETAILED DESCRIPTION OF THE PREFERRED EMBODIMENTS

Figure 1:
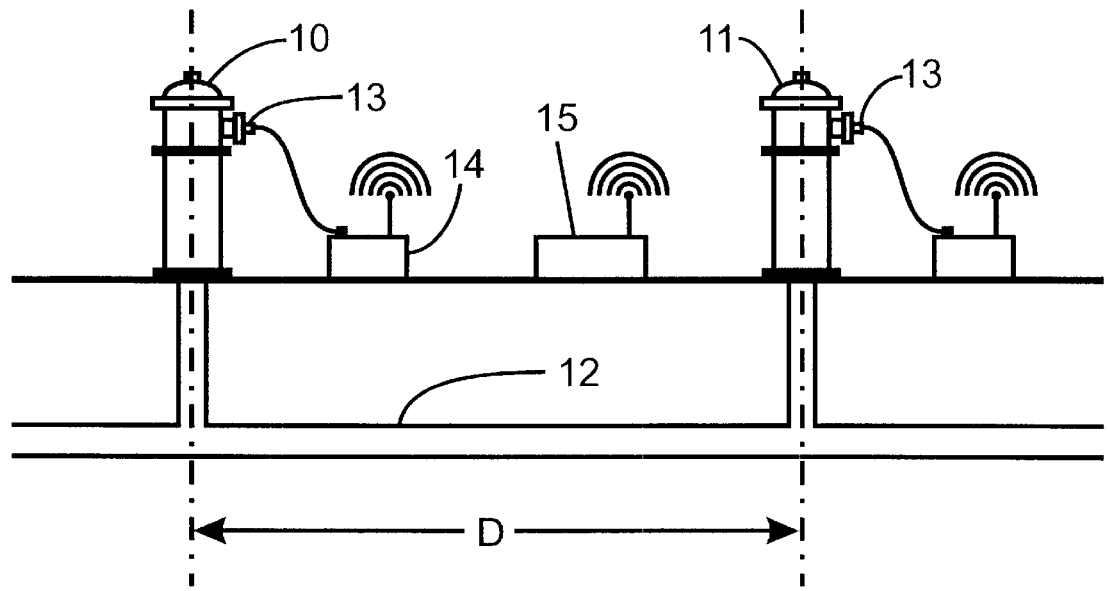
FIG. 1 is a schematic diagram of an arrangement for determining pipe wall thickness.

In FIG. 1, a pair of hydrants 10, 11 connected to a water distribution system 12, are spaced apart a distance D, typically in the order of 100 meters. A sensor, such as a hydrophone or accelerometer 13 is coupled to each hydrant 10, 11. A hydrophone picks up the pressure waves in the fluid medium, whereas an accelerometer picks up the vibrations in the wall of the pipe. The sensors are connected to RF transmitters 14, which communicate with a cross-correlator 15, which calculates the velocity of propagation of the signals between the hydrants. The coupled-mode signals can be generated by ambient noise in the pipe outside the hydrants 10, 11, or can be induced by, for example, opening a third hydrant outside the hydrants 10, 11 in order to induce an artificial leak.

In accordance with the invention, the propagation velocity of the coupled signals between the hydrants is determined, and from this the average pipe wall thickness between the hydrants 10, 11 can be calculated.

Figure 2:
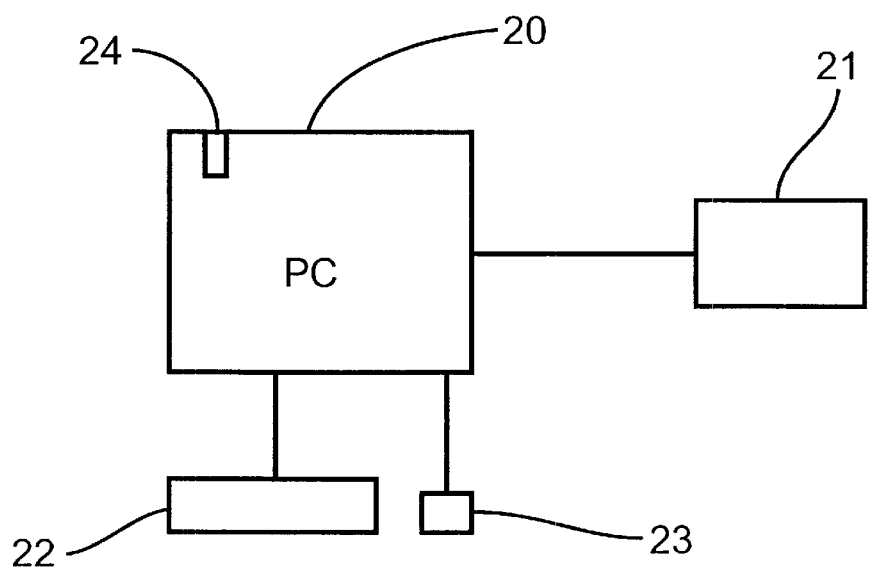
FIG. 2 is a block diagram of an apparatus for measuring average pipe thickness.

FIG. 2 shows a standard PC 20 (Personal Computer), monitor 21, keyboard 22, and mouse 23. The PC includes a sound card 24.

The object is to measure the propagation velocity of low frequency coupled mode signals between the hydrants 10, 11. This can be achieved either by making time-of-flight measurements, or preferably by using cross-correlation technique allowing for a time shift τ between the signals picked up at the two sensors to be determined. In time of flight measurements, the time is measured between the passage of a recognizable impulse between the sensors. In the cross-correlation technique, ambient sound, in the case of metal pipes typically a loud hissing noise, is recorded at the two locations, and the waveforms shifted in phase to achieve maximum correlation. The phase shift depends on the time it takes for the wave to travel between the sensors.

The signals from each sensor are recorded simultaneously using the stereo channels of a soundcard 24 of the PC 20 at any of the card's sampling frequencies, normally between 11,025 and 44,000 Hz. Recorded signals can be stored in either standard .wav or ASCII formats. The signals should be recorded using 16-bit resolution and the lowest possible sampling rate of the soundcard (e.g., 11,025 Hz). In most cases, it is sufficient to record signals for a duration between 30 to 60 seconds. In record mode, the volume control should be adjusted to utilize as much as possible of the soundcard's voltage range, without overloading it, in order to achieve a high signal-to-noise ratio.

In the case of metal pipes, the recorded signals sound like a loud hiss. By relatively shifting the channels to achieve maximum cross-correlation, the time lag between the two sensors can be measured. From this, knowing the separation distance, the propagation velocity can be calculated.

In the case of plastic pipes, the signals are typically below the audible range. However, it is possible to hear them on a PC by increasing the playback speed.

The frequency range of the recorded signals can be limited to suppress interfering noise components by applying low and high-pass digital filters at user-specified cutoff frequencies. The filters are of the recursive $4^{th}$ order Butterworth type. The square of the absolute value of the transfer function has the following forms for low and high-pass filters of this kind, respectively:

$$|H(f)|^2 = 1/(1+(\tan\pi f\Delta t/\tan\pi B\Delta t)^{2M})$$

$$|H(f)|^2 = 1/(1+(\cot\pi f\Delta t/\tan\pi B\Delta t)^{2M})$$

where f is frequency, B is filter cutoff frequency (or 3 dB point), Δt is the sampling interval, and M is number of poles or order of the filter.

The position propagation velocity can be calculated using the cross-correlation function. The latter is calculated in the frequency domain using the inverse Fourier transform of the cross-spectral density function instead of the usual shift-and-multiply method in the time domain. Calculating the cross-correlation function in the frequency domain is faster, and provides more effective "averaging out" of noise and a measure of signal-to-noise ratio via the coherence function.

Spectral analysis is preformed on the filtered (or unfiltered) signals to produce the following spectral estimates: (i) auto-spectra of the signals, (ii) coherence function, and (iii) cross-correlation function. The auto-spectra provide information about the frequency content of the signals. The coherence function provides a measure of the relationship between recorded signals—i.e., whether they were induced by the same source or not. The closer the coherence function to 1, the more related the signals. The cross-correlation function provides information about the time lag between signals, which in turn is used to calculate the propagation velocity.

Appropriate cutoff frequencies of low and high-pass filters depend on the type of pipe and sensor-to-sensor spacing and therefore no fixed rules can be specified. Normally, the cutoff frequencies should be selected so that they correspond to the frequency range where the amplitude of the autospectra of signals is significant and the coherence function is high.

Signals rarely contain frequency components above 1000 Hz in the case of metal pipes Therefore, in order to speed up digital filtering and spectral analysis of the signals, the sampling frequency of recorded signals can be reduced optionally to selected frequencies, e.g., 500, 1000, 2000, and 5000 Hz.

In order to understand how the propagation velocity is determined, it will be appreciated that the cross-correlation function between the time histories $f_1$ and $f_2$ of two random signals is defined as.

$$C_{12}(\tau) = \lim_{T \to \infty} \frac{1}{T} \int_o^T f_1(t) f_2(t+\tau) dt$$

where t is time and $\tau$ is time shift. Assuming that signals $f_1$ and $f_2$ represent the measured response at two locations due to a broad-band physical phenomenon propagating along a particular path in a nondispersive medium, the cross-correlation function can be used to obtain the time delay between the two signals. The delay corresponds the time shift $\tau_{max}$ that yields the maximum value for the cross-correlation function. In view of this interpretation, the cross-correlation function can be directly applied to the measurement of velocity knowing the distance between the two sensors. Similarity between the two signals $f_1$ and $f_2$ is essential for obtaining an accurate time delay—hence, the assumption of a nondispersive medium, i.e., one in which the propagation velocity does not vary with frequency. This is true for low frequency disturbances in the coupled propagation mode.

The invention can be applied as part of routine programs to monitor the integrity of municipal water distribution infrastructure and as part of maintenance management systems in every city. It also has important application in the monitoring of the integrity of oil and gas pipelines.

Although the present invention has been described and illustrated in detail, it is clearly understood that the same is by way of illustration and example and is not to be taken by way of limitation, the spirit and scope of the present invention being limited only by the terms of the appended claims.

I claim:

1. A method of measuring the wall thickness of a pipe carrying a fluid medium, comprising sensing disturbances in the pipe at two spaced locations, determining the propagation velocity of coupled propagation mode signals at low frequencies resulting from said disturbances, and calculating the average pipe wall thickness between said two locations from said propagation velocity and known constants for said pipe and fluid medium.

2. A method as claimed in claim 1, wherein said disturbances result from ambient noise existing in the pipe.

3. A method as claimed in claim 1, wherein said disturbances are induced by external action.

4. A method as claimed in claim 3, wherein said disturbances are induced by simulating a leak in the pipe.

5. A method as claimed in claim 4, wherein said propagation velocity is measured using a time-of-flight method.

6. A method as claimed in claim 4, wherein said propagation velocity is determined from cross-correlation and impulse functions, and phase angle method in the frequency domain.

7. A method as claimed in claim 1, wherein said average pipe wall thickness is determined from the relationship:

$$c = c_o \sqrt{\frac{1}{[1 + a(D/e)(K_w/E_\rho)]}}$$

where c is the propagation velocity of leak signals in the pipe, $c_0$ is the propagation velocity of sound in an infinite body of water equal to $\sqrt{K_w/\rho}$, $K_w$ is the bulk modulus of elasticity of the fluid medium, $\rho$ is density of the fluid medium and $E_\rho$ is the modulus of elasticity of the pipe material, D is internal diameter of the pipe, e is the thickness of the pipe wall, and $\alpha$ is constant that depends on the constraints of longitudinal movement of the pipe.

8. A method as claimed in claim 7, wherein said signals are detected using. accelerometers.

9. A method as claimed in claim 7, wherein said signals are detected using hydrophones.

10. A method as claimed in claim 1, wherein said pipe forms part of a water, gas, oil or other fluid distribution and transmission systems.

11. An apparatus for measuring pipe wall thickness, comprising a pair of sensors for detecting coupled mode signals at spaced locations on a pipe, and a processor for determining the propagation velocity of said coupled mode signals between said locations, said processor further determining the average pipe wall thickness between said locations from the propagation velocity and known constants for said pipe and fluid.

12. An apparatus as claimed in claim 11, wherein said sensors comprise hydrophones.

13. An apparatus as claimed in claim 11, wherein said sensors comprise accelerometers.

14. An apparatus for measuring pipe wall thickness as claimed in claim 11, wherein said processor is programmed to determine the average pipe wall thickness from the propagation velocity using the relationship:

$$c = c_o \sqrt{\frac{1}{[1 + a(D/e)(K_w/E_\rho)]}}$$

where c is the propagation velocity of leak signals in the pipe, $c_0$ is the propagation velocity of sound in an infinite body of the fluid medium equal to $\sqrt{K_w/\rho}$, $K_w$ is the bulk modulus of elasticity of the fluid medium water, $\rho$ is density of the fluid medium and $E_\rho$ is the modulus of elasticity of the pipe material, D is internal diameter of the pipe, e is the thickness of the pipe wall, and $\alpha$ is constant that depends on the constraints of longitudinal movement of the pipe.

15. A method of determining the type of pipe carrying a fluid medium, comprising sensing disturbances in the pipe at two spaced locations, determining the propagation velocity of coupled propagation mode signals at low frequencies resulting from said disturbances, and determining the type of pipe material from said propagation velocity and known constants for said pipe and fluid medium.

* * * * *